United States Patent [19]

Mather et al.

[11] Patent Number: 5,364,785
[45] Date of Patent: Nov. 15, 1994

[54] METHOD OF ISOLATING LUNG CELL LINE

[75] Inventors: Jennie P. Mather; Penelope E. Roberts, both of Millbrae, Calif.

[73] Assignee: Genentech, Inc., S. San Francisco, Calif.

[21] Appl. No.: 60,466

[22] Filed: May 11, 1993

Related U.S. Application Data

[63] Continuation of Ser. No. 919,994, Jul. 27, 1992, abandoned, which is a continuation of Ser. No. 479,130, Feb. 9, 1990, abandoned.

[51] Int. Cl.$^5$ .................. C12N 5/00; C12N 15/00; C12P 21/02; C12Q 1/00
[52] U.S. Cl. .................. 435/240.2; 435/4; 435/6; 435/29; 435/32; 435/172.1; 435/172.2; 435/172.3; 435/240; 435/31; 435/70.1
[58] Field of Search .............. 435/6, 29, 32, 172.1, 435/172.2, 172.3, 240.31, 4, 70.1, 948, 240.2

[56] References Cited

U.S. PATENT DOCUMENTS 4,885,238 12/1989 Reddel et al. .................. 435/29

FOREIGN PATENT DOCUMENTS 082974 7/1983 European Pat. Off. .
89/03994 5/1989 WIPO .

OTHER PUBLICATIONS

Freshney, "Bronchial and tracheal epithelium", *Culture of Animal Cells, A Manual of Basic Technique*, Alan R. Liss, Inc., New York, USA (1987).
Celis et al., *Electrophoresis 1989*, 10:76–100.
Lechner et al., *In vitro*, 18:633–642 (1982).
Lechner et al., *Journal of Tissue Culture Methods*, 9:43–48 (1985).

Primary Examiner—Robert J. Hill, Jr.
Assistant Examiner—Gian P. Wang
Attorney, Agent, or Firm—Renee A. Fitts; Wendy M. Lee

[57] ABSTRACT

A novel bronchial or bronchiolar epithelial cell from normal neonatal rat lung has been isolated, established and maintained for multiple passages in the absence of serum, without undergoing crisis or senescence. By careful manipulation of the nutritional/hormonal microenvironment we have been able to select, from a heterogeneous population, a single epithelial cell type which can maintain highly differentiated features in vitro. This cell type has characteristics of bronchiolar epithelial cells. A clonal line, RL-65, has been selected and observed for more than 2 years in continuous culture. It has been characterized by ultrastructural, morphological and biochemical criteria.

14 Claims, 4 Drawing Sheets

METHOD OF ISOLATING LUNG CELL LINE

This is a continuation of application Ser. No. 07/919,994 filed Jul. 27, 1992, now abandoned, which is a continuation of application Ser. No. 07/479,130, filed Feb. 09, 1990, now abandoned.

BACKGROUND OF THE INVENTION

1. Field of the Invention

This invention relates generally to a method of isolating a normal mammalian bronchial or bronchiolar epithelial lung cell; to the isolated mammalian epithelial lung cells produced by the method; to the use of the isolated mammalian epithelial lung cell for the production of proteins and as an assay system for pituitary factors which promote the growth of such mammalian epithelial lung cells. The unique method of isolating the lung cells results in novel bronchial or bronchiolar epithelial cells isolated from mammalian lung which grow in serum-free defined medium and which exhibit accelerated growth in the presence of mammalian pituitary extract.

2. Background and Prior Art

The lung is a complex organ composed of over 40 different cell types. Work on small cell carcinoma and recent advances in endocrinology have led to the recognition that the lung is the site of production of, and target tissue for a number of endocrine, paracrine and autocrine factors. While several tissue culture systems have been reported for primary culture of cells from the lung, specifically tracheobronchial epithelium (5,15,16,27,31), epithelial cell lines which can maintain their differentiated function in vitro have been difficult to establish without viral transformation or immortalization by transfection with various oncogenes. Reddel et al., PCT 89/03994 discloses human bronchial epithelial cells after viral transformation capable of growth in culture. These cells were transformed with SV40 or adenovirus-12 SV40 hybrid virus or with a recombinant plasmid containing portions of the Rous sarcoma virus. Clearly these cells are not the same as the normal cells of the present invention which do not contain such a transforming virus.

Serum is known to support the growth of many cell types, however it is complex and not well defined. In vivo, a cell would be exposed to the equivalent of serum only under special circumstances involving tissue injury and blood coagulation. In vitro, serum may not support the growth of some cell types, due to specific inhibition or a failure to provide an adequate concentration of stimulatory factors. For this reason we sought to utilize hormone-supplemented. serum-free medium as a method of selecting for specific cell types from the lung. Mather and Sato demonstrated that a serum-free hormonally defined medium for melanoma cells could be used to select for that same cell type when used as the culture media for a mixed cell population (23). Piltch et al were able to select for differentiated epithelial cells from rat thymus, and maintain these cells continuously in a defined serum-free medium supplemented with hormones (25). Loo and co-workers have described a serum-free, hormonally defined culture system for the establishment of a mouse embryo cell, selected from whole embryos. These cultures, when carried in the presence of serum, undergo a well-defined crisis or senescence (17). This senescence does not occur when these cultures are carried continuously in serum-free, hormonally defined culture. The inventors believe that non-transformed epithelial cell lines from normal tissue would be of great use in furthering our understanding of lung endocrinology and physiology. The inventors also believe that such cells would find use in the production of proteins and as an assay cell line responding to growth promoting factors thereby enabling the isolation of such growth promoting factors.

SUMMARY OF THE INVENTION

A novel bronchial or bronchiolar epithelial cell from normal neonatal rat lung has been isolated, established and maintained for multiple passages in the absence of serum, without undergoing crises or senescence. By careful manipulation of the nutritional/hormonal microenvironment we have been able to select, from a heterogeneous population, a single epithelial cell type which can maintain highly differentiated features in vitro. This cell type has characteristics of bronchial or bronchiolar epithelial cells. A clonal line, RL-65, has been selected and observed for more than 2 years in continuous culture. It has been characterized by ultrastructural, morphological and biochemical criteria. The strategy used for isolation and eventual establishment of cell lines from normal lung tissue is unique in that it utilizes a completely defined medium (in the absence of serum) to initially select for a specific type from the time of explant.

DESCRIPTION OF THE PREFERRED EMBODIMENTS

The lungs have multiple functions, but they have been difficult to study in vitro, largely because of the many diverse cell types. It was important to ascertain whether or not novel epithelial cell types of the lung could be isolated and established in vitro by careful manipulation of the nutritional/hormonal culture environment. We report here a serum-free, hormone-supplemented culture system which will initially select for a single epithelial cell type from normal, neo-natal mammalian (rat) lung. These cells will undergo multiple passages without crisis or senescence. A clonal cell line established in this fashion has been designated RL-65 and its properties are described below.

The distribution and frequency of ten morphologically distinct cell types has been described in the surface epithelium of the rat intrapulmonary airways (7). Eight of these cell types are epithelial, differentiating into secretory cells, ciliated cells, and cells whose main recognized function is to provide a large surface area for gas exchange. The maturation of the alveolar type 2 cell and the surfactant system is achieved prenatally, while maturation of the epithelium of the respiratory bronchioles and the small conducting airways occurs just after birth just prior to restructuring of the lung parenchyma and alveolarization (day 4–13) (3,22).

The RL-65 cell line, derived from the lungs of 5 day old rats, has phenotypic characteristics typical for cells of the airway epithelium. Studies are currently underway to further define the specific origin of this cell type. Evidence suggests it may be a type of progenitor cell with the capacity to differentiate along several pathways, depending on alterations in the cell culture microenvironment. This cell type is not readily observed during the first week in culture, but can easily be identified after 12 to 14 days in serum-free defined medium supplemented with 11F (see Table 1). This may be due to a change in morphology after time in culture, or its appearance may be facilitated by the death of most of the other cell types in the heterogeneous population. Alternatively, the late appearance of this cell type may be due to continued differentiation in vitro. Growth control and differentiation may be regulated by changes in culture conditions. The careful and timely addition/deletion of such components as BPE or retinoic acid, for example, may result in a culture condition in which cells either become committed to squamous differentiation and cornification, or further cell division.

TABLE 1

| Factor | 7F | 11F |
|---|---|---|
| Insulin (porcine) | 1 ug/ml | 10 ug/ml |
| Transferrin (human) | 10 ug/ml | 10 ug/ml |
| Epidermal Growth Factor | — | 5 ng/ml |
| Ethanolamine | $1 \times 10^{-4}$M | $1 \times 10^{-6}$M |
| Phosphoethanolamine | $1 \times 10^{-4}$M | $1 \times 10^{-6}$M |
| Selenium | $2.5 \times 10^{-8}$M | $2.5 \times 10^{-8}$M |
| Hydrocortisone | $2.5 \times 10^{-7}$M | $1 \times 10^{-9}$M |
| Forskolin | 1 uM | 5 uM |
| Progesterone | — | $1 \times 10^{-8}$M |
| Triiodothyronine | — | $5 \times 10^{-12}$M |
| Bovine lipoprotein | — | 0.5% |

Bovine pituitary extract (BPE) used at a concentration of 150 ug/ml protein concentration.
Retinoic acid (0.05 uM) + BPE is optimal for growth in 7F.

The RL-65 cells have a phenotype distinct from that reported for other types of long term cultures of lung cells, and other established lung cell lines. Bombesin, the gastrin releasing peptide found in neuroendocrine cells of the lung, was not produced in the RL-65. This suggests that they are probably not of neuroendocrine origin. The proteolytic activity of the RL-65, as well as PGE$_2$ production, points toward an important role in the detoxification of reactive compounds in the lung. This is further supported by the fact that this cell type has a large number of acetylated LDL receptors, perhaps for the purpose of scavenging and degrading extracellular molecules. It therefore may possess a "scavenger cell" pathway of acetylated LDL metabolism similar to that found in macrophages, endothelial cells and microglia (8,9,10,27).

The method of the present invention results in the production of novel mammalian epithelial lung cells. This method may be used to isolate such cells from the lung of any mammal, for example rat, human, rabbit, cow, and sheep. The method first incubates the fragments of lung tissue in serum free 11F medium for a period of from 10 to 90 days, more preferably, 15 to 50 days, and most preferably 21 to 35 days. The 11F medium is changed about every three days. This initial incubation is selective for the preferential survival of the epithelial lung cells of the present invention.

Following the initial incubation in 11F medium, the cultured lung cells are moved to medium containing pituitary extract (PE) or PE is added to the medium,. The pituitary extract may be present in an amount from 5 to 900 μg/ml, more preferably 50 to 300 μg/ml, and most preferably 100 to 500 μg/ml. The optimized basal medium (7F) for this cell line, RL-65, is Hams F12/DME plus insulin (1 μg/ml), human transferrin (10 μg/ml), ethanolamine ($10^{-4}$M), phosphoethanolamine ($10^{-4}$M), selenium $2.5 \times 10^{-8}$M), hydrocortisone ($2.5 \times 10^{-7}$M), and forskolin (5 μM). The addition of 150 μg/ml of bovine pituitary extract (BPE) to the defined basal medium stimulates a 5–20 fold increase in cell number, and a 10–100 fold increase in thymidine incorporation. The addition of retinoic acid results in further enhancement of cell growth and complete inhibition of keratinization.

The lung cells produced by the methods of the present invention may be grown in pituitary extract as described in Example 3. This extract may be made from any mammalian pituitary, including cow, human, rat, sheep, goat, horse, rabbit and pig.

In the presence of pituitary extract, the addition of retinoic acid further promotes the growth of the lung cells of the present invention. The concentration of retinoic acid may be between 0.0001 and 10μ molar more preferably between 0.01 and 1μ molar, and most preferably between 0.03 and 0.10μ molar.

The lung cells of the present invention may be used for the synthesis of proteins. The cells may be used in their untransformed state producing their normal homologous proteins with the homologous proteins isolated from the culture medium surrounding the cells, or from the harvested cells by conventional methods of protein isolation. Alternatively, the lung cells of the present invention may be transformed by an expression vector to produce a protein encoded by the expression vector. Any expression vector commonly used in mammalian tissues may be used, with the preferred vectors being those with known high expression in epithelial cells. Among the expression vectors suitable for use with the lung cells of the present invention are those described in U.S. application Ser. No. 07/441,574, filed Nov. 22, 1989, which is herein incorporated by reference.

The rat epithelial lung cell RL-65 is suitable for the production of its natural homologous proteins in serum free culture medium with these proteins recoverable from the medium by methods well known in the art of protein chemistry. The RL-65 cells may also be used with expression vectors as discussed for the production of heterologous proteins encoded by the expression vectors.

Among the natural protein products of the RL-65 cells is transforming growth factor beta and insulin-like growth factor I The use of expression vectors for the production of heterologous proteins includes lung surfactants, lymphokines, enzymes, hormones, hormone receptors, cytokines and lung cell specific antigens.

The cell line RL-65 has been deposited with the American Type Culture Collection (ATCC) in Rockville, Md., U.S.A. The ATCC designation for the RL-65 cell line is CRL 10354.

The lung cells produced by the methods of the present invention may be used to produce proteins which require the glycosylation patterns and other modifications such as palmitylation produced by lung cells. For example, the proteins secreted into the lung cell apical surface such as surfactant or protective enzymes. The lung cells may also be used to produce glycosylated proteins found in the vicinity of the basolateral surface of the cells. The lung cells may also be used to produce glycosylated or non-glycosylated proteins heterologous to the lung.

Methods of use for the lung cells of the present invention include the assay of growth promoting substances. Among the substances suitable for assay are the growth promoting substances found in pituitary extract. The cells of the present invention, for example the RL-65 cell line, may be used to detect the presence of the growth promoting substance during separation of the substance from contaminating molecules found in the pituitary extract. The separation may be by any commonly used methods separating the growth promoting substance on the basis of physical or chemical properties; for example, size, sedimentation value, charge, affinity binding or electrophoretic migration (see Example 3).

The use of the lung cells as an assay system for a growth promoting substance is accomplished by detecting the growth of the cells. Among the easiest properties to evaluate are the number of cells present after a reasonable period of incubation in the presence of the growth promoting substance. Alternatively, measures of cell metabolism associated with growth may also be determined to assay for the presence of the growth promoting substance. For example, the synthesis of DNA and the incorporation of a radioactive nucleotide are preferred methods of determining responsiveness to a growth promoting substance. Among the preferred radio nucleotides is tritiated thymidine.

The role of vitamin A in the control of cell proliferation and differentiation has been well documented, both for cells of the tracheobronchial epithelium (4,19,20,21,28,32,33), as well as cells from other tissues (1,4,18). Experiments to date have demonstrated, both at the ultrastructural and light microscopy level, the striking inhibitory effect of retinoic acid on keratinization in the RL-65. Moreover, at concentrations varying from 0.01 $\mu$M to 0.5 $\mu$M, retinoic acid had a marked stimulatory effect on cell growth. Bovine pituitary extract has been demonstrated to be stimulatory for growth in a number of culture systems (2,10,14,26,29), including the airway epithelium. Studies on the effect of pituitary extract on RL-65 have shown 5 to 20 fold increase in growth. We have tested the known and commercially available pituitary growth factors, none of which, by themselves or in combination, have demonstrated a growth effect equal to that of BPE. Moreover, since the extract is a homogenate of whole pituitaries, factors found in clotted blood serum, such as PDGF, and the hematopoietic factors IL-1 and IL-2 were also tested and found not to have stimulatory activity. Experiments are currently underway to isolate the active fractions in bovine pituitary extract and to identify what may be a novel growth factor for airway epithelial cells.

Isolation Procedure

We have demonstrated that, because each cell type, even within the same region of the same tissue requires a different combination or concentration of nutrients, hormones and/or growth factors, a carefully tailored serum-free environment will lead to the isolation and identification of new types of cells from the lung which have not previously been established in vitro. This will then provide the opportunity to isolate and characterize the unique gene products of these specific lung cells, to investigate cell-type specificity of physiology and gene control, and to study normal differentiated function of these cells in vitro

Materials and Methods

Animals.

5 day old male Sprague Dawley rats used for these experiments were obtained from Simonsen Labs, Gilroy, Calif.

Materials.

Dulbecco's Modified Eagle's Medium, high glucose (DME), and Ham's F12 medium (F12) were obtained in powder form from Grand Island Biological Co.(GIBCO), Grand Island, N.Y.; porcine insulin (pIns), human transferrin (hTF), hydrocortisone (HC), progesterone (P), ethanolamine (Eth), phosphoethanolamine (PEth), triiodothyronine (T3), and soybean trypsin inhibitor (STI), were obtained from Sigma Chemical Co., St. Louis, Mo.; trypsin (0.05%+0.0.53 mM EDTA) was obtained from GIBCO; epidermal growth factor (EGF) from Collaborative Research, Waltham, Mass.; forskolin (FK) was obtained from Calbiochem, La Jolla, Calif.; bovine lipoprotein (predominantly HDL) (Excyte®) was obtained from Miles Laboratories, Napierville, Ill.; sodium selenite (Sel) from Johnson Matthey Inc. (Aesar, Seabrook, N.H.); whole mixed sex bovine pituitaries were obtained from Pel Freeze, Rogers, Ark.; human plasma fibronectin (fbn) was obtained from Bethesda Research Labs (GIBCO), Bethesda, Md.; tubulin, desmin and vimentin MAB's were obtained from Chemicon International, Los Angeles, Calif.; rabbit antihuman keratin and rabbit antichicken actin were obtained from Polysciences, Warrington Pa.; fluorescein isothiocyanate (FITC) conjugated, F(ab 1)2 fragments of goat antimouse and antirabbit IgG (H and L chains specific) were obtained from Jackson ImmunoResearch Laboratories, West Grove, Pa. DiI-Ac-LDL was obtained from Biomedical Technologies, Stoughton, Mass. The following pituitary factors were obtained from Sigma Chemical Co.: Growth hormone (gh), follicle stimulating hormone (FSH), thyroid stimulating hormone (TSH), human luteinizing hormone (hLH), human prolactin (hPRL), adrenocortocotropic hormone (ACTH), oxytocin (OXY), vasopressin (ADH), $\alpha$ and $\beta$ melanocyte stimulating hormone ($\alpha$, $\beta$, MSH), $\beta$lipotropin fragments ($\beta$lipo), $\alpha$, $\beta$, $\gamma$ endorphin (END). Fibroblast growth factor (FGF) was obtained from Collaborative Research. Two-dimensional gels were run and computer analyzed by Protein Databases Inc. (Huntington Station, N.Y.). Radiochemicals were purchased from New England Nuclear (Boston, Mass.).

Recombinant human TGFβ was supplied by Genentech.

Culture Media and Conditions

DME and Ham's F12 (1:1 w/w) were dissolved in Milli-Q water, and supplemented with 1.2 g/L NaHCO3, 0.4g/L glutamine and 15 mM Hepes. Hormones, trace elements, vitamins and phospholipids used to supplement the serum-free medium are shown in Table 1. All of these factors are prepared as sterile stock solutions at 100-1000 fold final concentration and added to the medium just prior to use. Bovine pituitary extract (BPE) was prepared by the method of Tsao et al (29). Cells were incubated in a 5% $CO_2$/95% air, $H_2O$ saturated atmosphere at 37° C.

EXAMPLE 1

Establishment of Lung Cell Line

Primary Culture.

Five day old male Sprague Dawley rats were sacrificed by $CO_2$ asphyxiation, the lungs removed, the trachea excised, and the entire lung washed briefly in serum free medium containing 20 μg/ml Gentamycin. The tissue was minced into fragments which were then resuspended in serum-free medium containing 0.05 % (w/v) collagenase-dispase and incubated for 30-45 minutes at 37° C. The tissue fragments were washed twice with serum free medium and allowed to settle for 15 minutes after which time the supernatant was removed. The fragments were dispersed by repetitive pipetting in serum-free, hormone supplemented medium (11F, see Table 1) and aliquoted into fibronectin-coated 60 mm tissue culture dishes. Medium was changed every three days and the cultures maintained in 11F medium for 1 month. At this point bovine pituitary extract (BPE), at 150μg/ml, was added. Colonies became densely packed monolayers within 7-10 days from the day of addition of BPE, and were passaged at this stage.

Serial Passage.

Highly cornified colonies from 60 mm dishes were initially passaged by several trypsinizations (0.05% trypsin-0.53 mM EDTA) for 10' each at 37° C. After neutralization with soybean trypsin inhibitor (STI, 1 mg/ml), cells were washed twice by centrifugation in serum-free F12/DME to remove residual STI, and plated in fibronectin-coated 12-well trays (usually 1 60 mm dish/well) containing 11F supplemented with BPE medium. Cells were subsequently passaged at near-confluency, and seeded into sequentially larger dishes at each passage. Continuous culture was then maintained by passaging at near confluency and at a high seeding density (1:1 or 1:2 split ratio). At no time after the addition of the BPE did the cells undergo a reduction in growth rate or "crisis".

Establishment of a Cloned Lung Epithelial Cell Line.

Lung epithelial cells grown continuously in this way for several months do not require that the dishes be fibronectin coated for attachment. Cloned populations were selected by plating 100-500 cells in a 100 mm dish containing 15% conditioned 11F medium and changing the medium every 3 days. By day 10, colonies were of sufficient size to be cloned by trypsinizing in 6 mm stainless steel cloning rings, (penicylinders, Bellco). Each colony was then seeded into one well of a 24-well tray, grown to near confluency, and the entire well passaged into sequentially larger surface areas at each trypsinization until stock cultures could be maintained in 100 mm dishes. All of the colonies picked had a similar morphology. One of these clones, designated RL-65, was chosen for further characterization, and the optimal nutrient and hormonal requirements were determined. This cell line has been carried in continuous culture for more than 2 years. The RL-65 stocks are currently maintained by passaging every 4-6 days at a 50-200 split ratio.

Growth and Morphology of Primary Cultures.

The initial cell population, which attaches and spreads after plating the dispersed lung tissue, is heterogeneous. By choosing very specific initial culture conditions, followed by a growth medium, we have been able to select against a large number of cell types in the lung as well as allow the survival of the particular cell type we designate as RL-65. If serum is present initially, a heterogeneous culture is obtained and, with time, the culture is eventually overgrown by fibroblastic cell types. If bovine pituitary extract is present initially, even in the absence of serum, a fairly heterogeneous population of non-fibroblastic cells is evident and the population remains heterogeneous with time. The protocol described first uses a serum-free, defined medium (11F, see Table 1) to allow the survival, but not growth of the desired cell type, while not supporting the survival of the majority of cells in the original culture. The selection seems to occur both by providing an environment inadequate for the growth of some cells while actively inhibiting the survival/growth of others. This is followed by the addition of a critical mitogenic component (BPE), and the subsequent optimization of a medium for enhanced growth of the surviving cells. If the optimized medium (7F and BPE) is used in the initial protocol, a diverse population of cells is supported, which may obscure or outstrip the growth of the desired cell type. Thus, in selecting for, and in the establishment of the RL-65 cell, the chronology of events and the timely addition/deletion of the proper supplements is critical.

Continuous Culture.

Figures 1A, 1B:
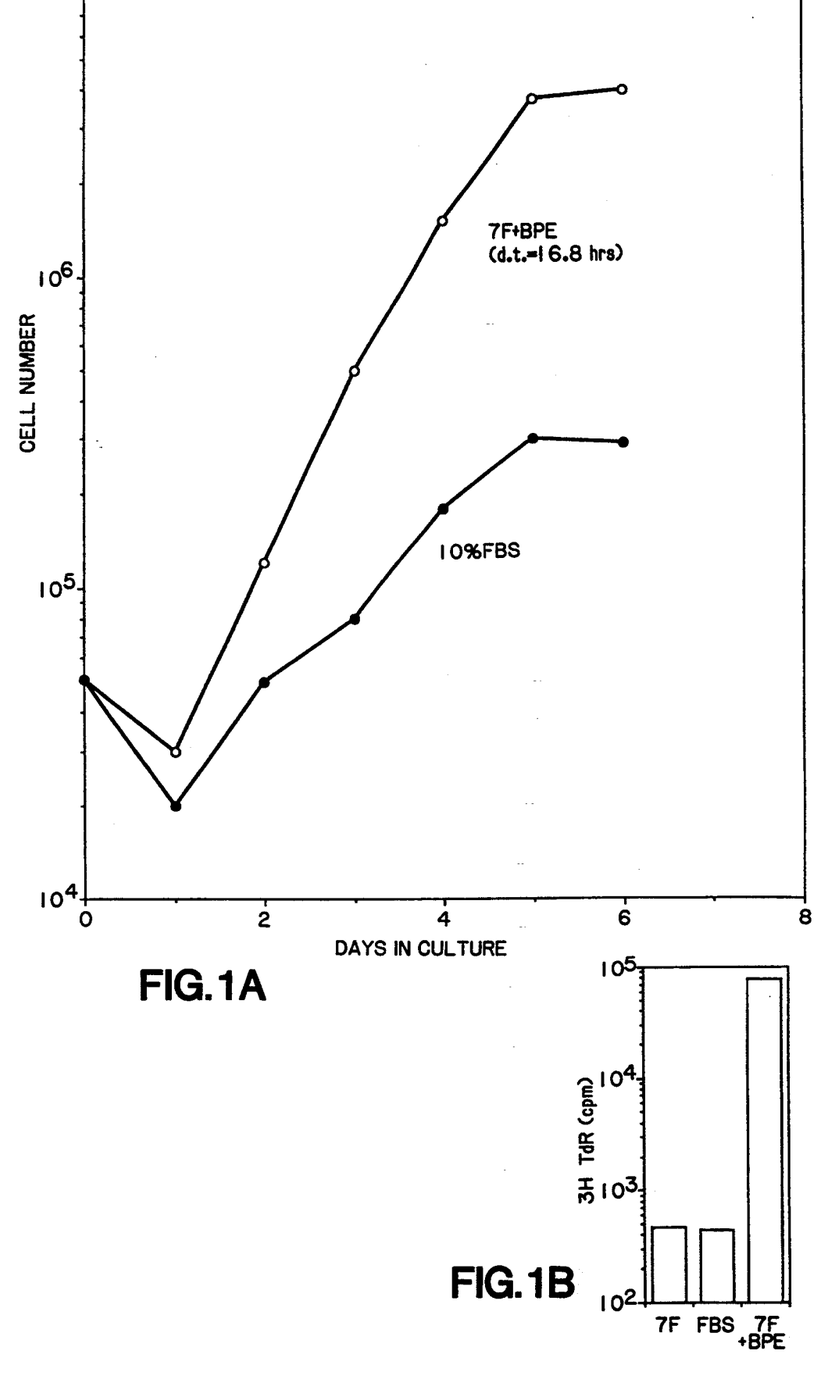
FIG. 1A and 1B Growth of RL-65 in 7F+BPE vs 10% FBS. Cells were plated at $5 \times 10^4$ cells/21 cm$^2$ and counted on day 5. Inset: thymidine incorporation 72 hrs. after plating (see Methods for definitions).
Figure 2:
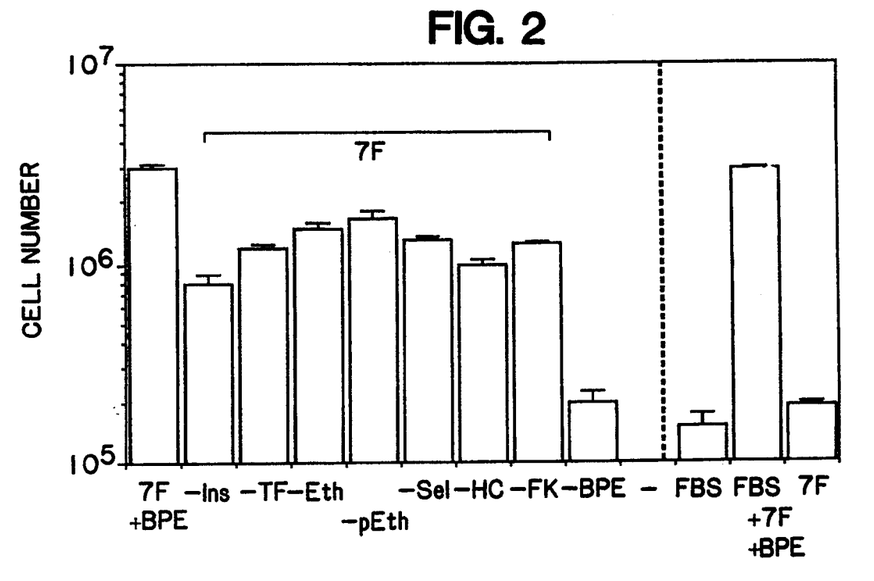
FIG. 2 Effect of FBS, BPE, and individual growth factors in 7F on growth of RL-65. Concentrations are given in Table 1. Each factor and BPE was omitted individually and growth in the remaining components compared with growth in the optimal medium (7F+BPE). Also compared: 10% FBS in presence and absence of 7F+BPE (±sem).

Long term cultures were established by serially passaging at high density in 15% (v:v) conditioned/fresh 11F medium and BPE, supplemented with fresh 11F and BPE. These cultures became progressively more homogeneous even prior to cloning, and grew without fibronectin pre-coating of the dish. Optimal growth for the RL-65 clonal line was found to require only pins, hTF, eth, Peth, Sel, HC, FK (7F) and BPE at the concentrations shown in Table 1. The remaining factors, progesterone, T3, bovine lipoprotein and EGF, showed no further growth stimulation in the presence of the optimal 7F and BPE supplements and were omitted. RL-65 exhibited a doubling time of 17 hours, and had a 50-100 fold increase in $^3H$ thymidine incorporation in this medium (FIGS. 1A and 1B). Neither 7F, in the absence of bovine pituitary extract, nor pituitary extract alone could stimulate cell division to the same extent as the combination. Each of the 8 components used in the optimized medium has proved to be essential to achieving an optimal doubling time, BPE being the most crucial. 10% Fetal bovine serum alone did not stimulate to optimal growth levels. This may be due less to inhibitory substances in serum than to a lack of essential growth factors, either absent in serum, or not provided in the necessary concentration. In the presence of those factors required for growth, serum was not inhibitory (FIG. 2).

Figure 3:
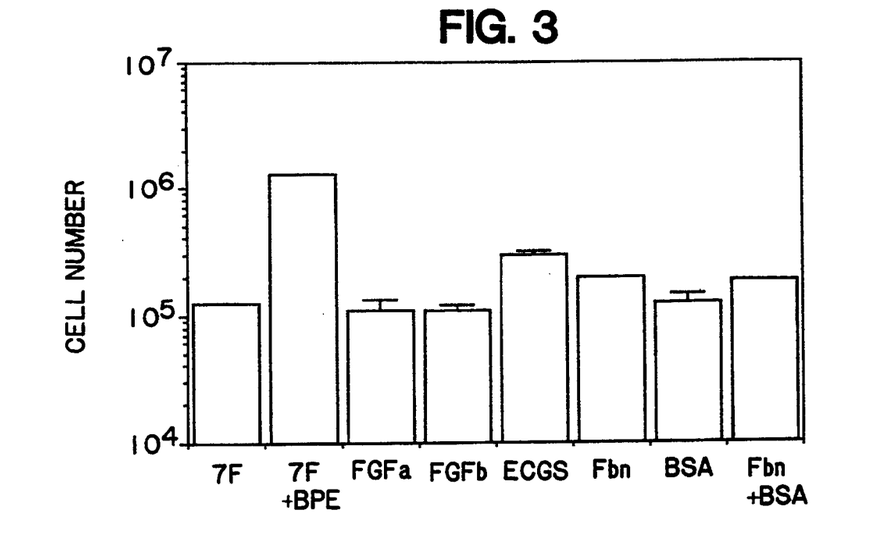
FIG. 3 Effect of FGF acidic (FGFa, 5ng/ml), FGF basic (FGFb, 5ng/ml), endothelial cell growth supplement (ECGS, 100 μg/ml), fibronectin (Fbn 30 ug/21 cm$^2$), and bovine serum albumin (BSA, 15 μg/ml).
Figure 4A:
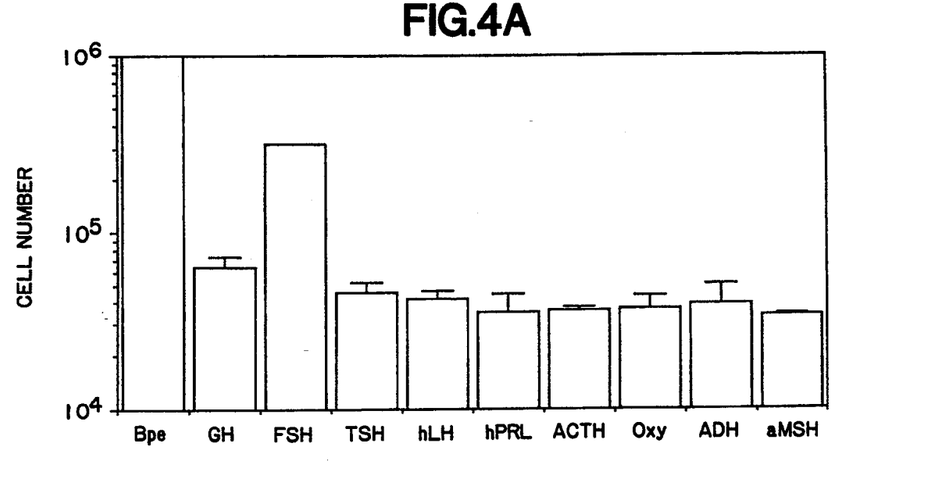
FIGS. 4A and 4B Effect of pituitary growth factors on growth of RL-65. Each factor was added in the presence of 7F and compared to 7F supplemented with BPE or 7F alone (±sem). GH,1 μg/ml; FSH, TSH, 10 μg/ml; hLH, hPRL, 5 ng/ml; ACTH, Oxy, ADH, aMSH, βMSH,10 ng/ml, βlipotropin fragments, β, α, ∂) endorphin, 100 ng/ml, FGF, 3 ng/ml.
Figure 4B:
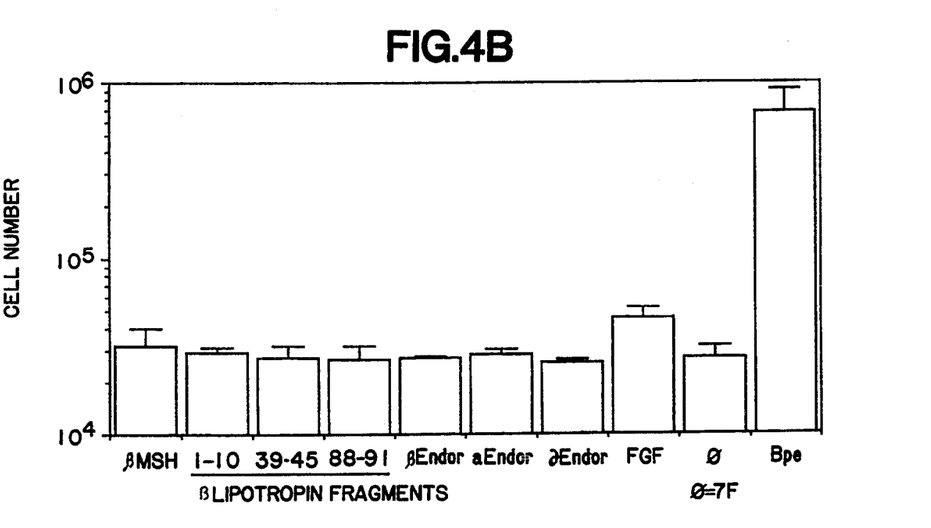

BSA, fibronectin, endothelial cell growth supplement (ECGS) and fibroblast growth factor (FGF), all present in pituitary extract, could not alone, or in combination, account for the response to BPE (FIG. 3). Initial screening of all known and commercially available pituitary factors, at varying concentrations, alone and in combination, demonstrated no stimulation over control (FIGS. 4A and 4B). While a crude preparation of FSH appeared to stimulate growth (FIGS. 4A and 4B), 2 different more highly purified preparations had no growth stimulatory activity.

Nutrient and Hormone Interactions

Figure 5:
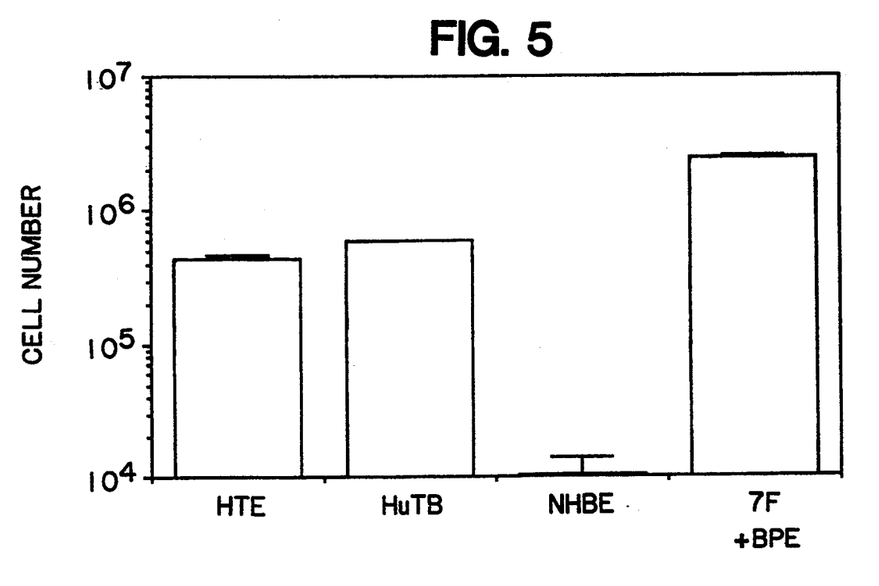
FIG. 5 Growth of RL-65 in various basal media formulations supplemented with hormones and growth factors. Media composition was based on published reports: HTE, hamster trachael epithelial (33); NHBE, normal human bronchial epithelial (15); HuTB, human tracheobronchial (5).

Serum-free media was prepared by supplementing F12/DME with a mixture of hormones, growth factors and trace elements. F12/DME, mixed 1:1, was initially selected as the basal medium because of its widespread use in supporting the growth of a large variety of mammalian cells. Basal media formulations previously shown to be optimal for hamster and human tracheal epithelial cells, and human bronchial epithelial cells were either inhibitory or not optimal for the growth of RL-65 (FIG. 5). These included some of the MCDB media (MCDB 151,152,153, 301 and 302) originally developed in Ham's lab for the growth of human keratinocytes (29), and modified by other labs for the growth of airway epithelial cells. Other cell types of the lung, such as the epithelial mink lung cell line, were unable to grow or survive in the optimized RL-65 medium.

The addition of 0.05 $\mu$uM retinoic acid further increased cell number in the presence, but not in the absence of BPE.

EXAMPLE 2

Characterization of Cell Line RL-65

Indirect Immunofluorescence.

Cells were grown to near confluency on 12 mm glass coverslips. The coverslips were moved to fresh serum-free F12/DME and paraformaldehyde added to a final concentration of 2%. After 20' the coverslips were washed with phosphate buffered saline (PBS), and placed in 0.1M Glycine for an additional 20'. After washing 2× in PBS, 1% Triton-X 100 was added and left on for 6'. The coverslips were then washed 2× with PBS and exposed to the first antibody (diluted 1:25) for 30' at 37° C. After rinsing 4× in PBS (5'/rinse), the second antibody (1:10) was added and the above procedure was repeated. The coverslips were then drained, air dried, mounted in Aquamount, and examined with a Nikon Microphot FX epiflourescence microscope.

Electron Microscopy.

Near-confluent cultures of primary lung cells or the established RL-65 line were prepared for electron microscopy by washing the cells with serum-free F12/DME, diluting the medium 1:1 with 2.5% gluteraldehyde in 0.2M phosphate buffer (pH 7.2), then fixing overnight in 2.5% gluteraldehyde. Alternatively, cells were grown on collagen coated Transwell membrane inserts (Costar) in 6-well trays, and fixed as above. Cultures were postfixed in 1% buffered $O_5O_4$, dehydrated in alcohol, and embedded in Polybed (Polysciences, Inc.). Sections cut on a Reichart OmU3 ultratome were stained in 3% aqueous uranyl acetate at 50° C. for 1 hr. and examined with a Phillips 300 microscope.

Quantitative Assay of Growth.

Cells were seeded into 60 mm dishes and counted on day 5. Cells were dispersed by trypsinization and counted with a Coulter counter (Model ZF). Viability was determined by the ethidium bromide/acridine orange method (24). Thymidine incorporation studies were done at 24, 48, and 72 hours after plating. Cultures which were seeded at $5 \times 10^4$ cells/60 mm dish (4 ml/dish) were pulsed for 3 hrs. with 1 uCi/ml $^3$H thymidine. Dishes were rinsed 1× in serum-free F12/DME, then rinsed 2× in 5% trichloroacetic acid (TCA). One ml of 0.1N NaOH was added to each dish and after 15 minutes 0.5 ml from each dish was transferred to a 7.5 ml mini-vial. To each vial was added 3.5 ml of scintillation fluid and 200 $\mu$l of 40% acetic acid. Vials were counted for 1 minute each in a Beckman 3800 counter.

Ultrastucture.

The most prominent feature of the primary cultures grown in 11F supplemented with BPE are expanded ER and numerous microvilli. Additionally, there are many microfilaments, connected together by desmosomes on cellular processes. Cells grown in the presence of retinoic acid had a markedly different morphology exhibiting more densely packed colonies and a complete absence of cornification or keratinization.

In the presence of retinoic acid (0.05 $\mu$M), the epithelium resembles a low non-keratinized transitional or squamous epithelium. As in a typical epithelium of this type, basal cells are cuboidal in shape and apical cells more squamous. The absence of retinoic acid in the culture medium totally alters the morphological appearance of the cultures. Cells grown on membrane inserts exhibit an epithelium which is very obviously keratinized. In cultures which have been grown long enough to be a few cells deep, the apical cells (distal to the membrane) become flattened, whereas the basal cells are cuboidal. Desmosomes are prominent as are numerous epidimal filaments. Filaments are observed throughout the epithelium, even in the basal cells.

When cultures in the absence of retinoic acid are allowed to grow longer, the epithelium becomes more stratified and so highly keratinized that the apical cells die. Sections cut parallel to the filter membrane reveal elaborate networks of epidermal filaments. Viewed at high magnification, the organelles of this highly differentiated, keratinized, stratified epithelium are seen to be highly developed. Desmosomes, indistinguishable from normal skin, are associated with typical tonofilaments. Large granules, similar to keratinophylan granules are also observed in these cells, especially in cells near the apical surface of the epithelium. Epidermal filaments are particularly well developed in these cells. In sections cut parallel to the filter membrane, they appear in semiregular patterns of swirls and circles.

Phenotype of RL-65.

The primary and secondary lung cultures, as well as the established cell line RL-65, grown in the absence of retinoic acid, exhibit characteristics typical of epithelial cells. The cells were found to contain alpha keratin, as determined by indirect immunoflourescence, as well as other cytoskeletal proteins, actin, desmin, vimentin and tubulin. In addition, the cells reacted positively with antisera against the rat cell attachment proteins fibronectin and laminin.

EXAMPLE 3

Lung Cell Assay System

Mammalian epithelial lung cells produced by the method of Example 1 may be used to assay for the presence of growth promoting substances. The cell is used as a biological indicator with the growth of the lung cell serving as the assay for the presence of the growth promoting substance during the purification process. The lung cell may be used to assay fractions from any commonly practiced purification procedures, such as ion exchange chromatography, affinity chromatography, isoelectric focusing, gel exclusion chromatography, centrifugation, electrophoresis and other methods which separate various molecules on the basis of their physical or chemical properties. Specific methods suitable for separating the growth promoting substances are more fully described in volume 1 or 2, Current Protocols in Molecular Biology, Wiley Interscience (1989), herein incorporated by reference. Chapter 10, Analysis of Protein, specifically describes preferred methods for separating protein.

One type of growth promoting factor which may be purified by the lung cells of the present invention is the pituitary extract factor which promotes growth of the epithelial lung cells of Example 1. For example, if the lung cells are rat lung cells and the pituitary extract is bovine, the following illustrates the procedures to be used. The rat lung cell utilized is designated RL-65.

I. METHODS

A. 108S Pituitary Extract Preparation

Bovine pituitary extract (BPE) is made by homogenizing 105 g mixed sex bovine pituitaries in 250 ml cold 0.15M NaCl for 10 minutes in a blender. The homogenate is then transferred to a cold beaker and stirred for 90 minutes at 4° C. Next it is centrifuged at 4° C. for 40 minutes at $9800 \times g$. The pellet is discarded and the supernatant is aliquoted into 50 ml polypropylene tubes and at this point can be stored at $-20°$ C. Aliquots are filtered through a $0.8\mu$ filter and then subjected to ultracentifugation at $108,000 \times g$ for 3 hours. The supernatant is carefully decanted, filter sterilized through a $0.22\mu$ filter, and stored in 5 ml polypropylene "snap-cap" tubes at $-70°$ C.

B. Bioassay

1. Cell Number

Cells are plated in 60 mm dishes (4 ml/dish) at a seed density of $5 \times 10^4$ cells/dish and counted on day 5 using a Coulter Counter ZF. Alternatively, cells are plated in 35 mm wells (6-well trays, 2 ml/well) at a seed density of $2.5 \times 10^4$ cells/well and counted on day 5.

2. Thymidine Incorporation

Thymidine incorporation studies were done at 24, 48 and 72 hours after plating. Cultures which were seeded at $5 \times 10^4$ cells/60 mm dish (4 ml/dish) or at $2.5 \times 10^4$/well (6-well tray, 2 ml/well) were pulsed for 3 hours with 1 uCi/ml $^3$H thymidine. Dishes were rinsed $1 \times$ in serum-free F12/DME, then rinsed $2 \times$ in 5% trichloroacetic acid (TCA). One ml of 0.1N NaOH was added to each dish and after 15 minutes 0.5 ml from each dish was transferred to a 7.5 ml mini-vial. To each vial was added 3.5 ml of scintillation fluid and 200 $\mu$l of 40% acetic acid. Vials were counted for 1 minute each in a Beckman 3800 counter.

| II. PURIFICATION SCHEME Purification of Bovine Pituitary Extract (108S) Mitogenic Activity on RL-65 Rat Lung Cells | | |
|---|---|---|
| | Recovery % Bioactivity | Recovery % Protein Content |
| Gel filtration, BioGel P-300 | 20% | 40% |
| Affinity chrom.: anti-BSA | 100% | 70% |
| Affinity chrom.: Heparin-Seph | 100% | 95% |
| Affinity chrom.: Con A-Seph | 100% | 95% |
| Ion Exchange: HTP | 56% | 5–10% |
| Expected purification of 108S on combined HTP/anti-BSA column is 50–100 fold | 56% | 0.5% |

A. P-300 gel filtration. To concentrate on collecting fractions in the 50–100 Kd range, where mitogenic activity exists.
B. Heparin-sepharose and conA column to remove growth factors and attached proteins.
C. αBSA IgG column. To remove albumin and have a mitogenic eluate which can be further purified by use of HPLC.
D. Hydroxylapatite or HPLC.

Variations of the above scheme may be developed by substituting or adding other types of chromotography and by varying the ionic strength and pH of the solvent.

The foregoing written specification is considered to be sufficient to enable one skilled in the art of cell biology and protein chemistry to practice the invention. The present invention is not to be limited in scope by the cell line deposited, since the deposited embodiment is intended as an illustration of certain aspects of the invention and that many other similar cells may be isolated using the methods of the present invention on mammalian lung tissue. The deposit of the cell line herein does not constitute an admission that the written description herein is inadequate to enable the practice of any aspect of the invention, including the best mode, nor is it to be construed as limiting the scope of the claims to the specific cell deposited. Indeed, various modifications of the invention in addition to those shown and described in the specification will become apparent to those skilled in the art and fall within the scope of the appended claims.

All citations noted are herein incorporated by reference.

1. BREITMAN, T. R., S. E. SELONICK, and S. J. COLLINS. Induction of differentiation of the human promyelocytic leukemia cell line (HL-60) by retinoic acid. Proc. Natl. Acad. Sci. USA. 77: 2936–2940, 1980
2. BROCKES, J. P., and M. C. RAFF. Studies on cultured rat schwann cells 2. Comparison with a rat schwann cell line. In Vitro (Rockville). 15: 772–778, 1979.
3. BURRI, P. H. The postnatal growth of the rat lung. Ill. Morphology. Anat. Rec. 180: 77–98, 1974.
4. CHOPRA, D. P. and B. A. FLAXMAN. The effect of vitamin A on growth and differentiation of human keratinocytes in vitro. J. Invest. Dermatol. 64:19–22, 1975.
5. CHOPRA, D. P., J. SULLIVAN, J. J. WILLE, and K. M. SIDDIQUI Propagation of differentiating normal human tracheo-bronchial epithelial cells in serum-free medium. J. Cell Physiol. 130:173–181, 1987.
6. CUTTITTA, F., D. N. CARNEY, J. MULSHINE, T. W. MOODY, J. FEDORKO, A. FISCHLER, and J. D. MINNA. Bombesin-like peptides can function as autocrine growth factors in human small-cell lung cancer. Nature. 316: 823–826, 1985.
7. EVANS, M. J., and SHAMI, S. G. Lung cell kinetics. In: Lung Cell Biology, edited by D. Massaro, New York, N.Y.: Marcel Dekker, 1989, p. 1–89.

8. GARRELS, J. I. Two dimensional gel electrophoresis and computer analysis of proteins synthesized by clonal cell lines. *J. Biol. Chem.* 254: 7961-7966, 1979.

9. GARRELS, J. I., J. T. FARRAR, and C. B. BURWELL IV. The QUEST system for computer-analyzed two-dimensional electrophoresis of proteins. In: *Two Dimensional Gel Electrophoresis of Proteins: Methods and Applications*, edited by J. E. Celis and R. Bravo, New York: Academic Press, 1984, p. 38.

10. GITHENS, S., J. A SCHEXNAYDER, K. DESAI, and C. L. PATKE. Rat pancreatic interlobular duct epithelium isolation and culture in collagen gel. *In Vitro.* 25 (8): 697-688, 1989.

11. GOLDSTEIN, J. L. and M. S. BROWN. Artheroslerosis: the low-density lipoprotein receptor hypothesis. Metabolism. 26(11): 1257-1275, 1977.

12. GOLDSTEIN, J. L., Y. K. HO, S. K. BASU, and M. S. BROWN. Binding site on macrophages that mediates uptake and degradation of acetylated low density lipoprotein, producing massive cholesterol deposition. *Proc. Natl. Acad. Sci.* 76(1): 333-337, 1979.

13. GUILIAN, D. and D. G. YOUNG. Brain peptides and glial growth. II. Identification of cells that secrete glia-promoting factors. *J. Cell Biol.* 102: 812-820, 1986.

14. KABALIN, J. N., D. M. PEEHL, and T. A. STAMEY. Clonal growth of human prostatic epithelial cells is stimulated by fibroblasts. *Prostate.* 14 (3): 251-264, 1989.

15. LECHNER, J. F., A. HAUGEN, I. A. McCLENDON and E. W. PETTIS. Clonal growth of normal adult human bronchial epithelial cells in serum-free medium. *In Vitro.* 18: 633-642, 1982.

16. LEE, T. C., R. WU, A. R. BRODY, J. C. BARRETT and P. NETTESHEIM. Growth and differentiation of hamster tracheal epithelial cells in culture. *Exp. Lung Research.* 6: 27-45, 1984.

17. LOO, D. T., J. I. FUQUAY, C. L. RAWSON, and D. W. BARNES. Extended culture of mouse embryo cells without senescence: inhibition by serum. *Science* .236: 200-202, 1987

18. LOTAN, R. Effects of vitamin A and its analogs (retinoids) on normal and neoplastic cells. Biochim. Biophys. Acta. 605: 33-, 1980.

19. MARCHOK, A. C. and R. C. KLANN. Effects of retinoic acid on cell proliferation and cell differentiation in a rat tracheal epithelial cell line. *Cell Tissue Kinet.* 15: 473-482, 1982.

20. MARCHOK, A. C. J. C. RHOTON, R. A. GRIESEMER and P. NETTESHEIM. Increased in vitro growth capacity of tracheal epithelium exposed in vivo to 7,12-dimethylbenz(a)anthracene. *Cancer Research.* 37: 1811-1821, 1977.

1. MASS, M. J., P. NETTESHEIM, T. E. GRAY, and J. C. BARRETT. The effect of 12-0-tetradecanoylphorbol- 13-acetate and other tumor promoters on the colony formation of rat tracheal epithelial cells in culture. *Carcinogenesis* .5: 1597-1601, 1984.

22. MASSARO, G. D., and D. MASSARO. Development of bronchiolar epithelium in rats. *Am. J. Physiol.* 250: R783-R788, 1986b.

23. MATHER, J. P. and G. SATO. Hormones and growth factors in cell cultures: problems and perspectives. In: *Cell Tissue and Organ Cultures in Neurobiology.*, New York: .Academic Press, p. 619-630, 1978

4. PARKS, D. R., V. M. BRYAN, V. T. OI, and L. A. HERZENBERG. Antigen-specific identification and cloning of hybridomas with a fluorescence-activated cell sorter. *Proc. Natl. Acad. Sci* USA. 76: 1962-1966, 1979.

25. PILTCH, A., P. NAYLOR and J. HAYASHI. A cloned rat thymic epithelial cell line established from serum-free selective culture. *In Vitro* 24: 289-293, 1988.

6. REZNIKOFF, C. A., L. J. LORETZ, D. M. PESCIOTTA, and T. D. OBERLEY. Growth kinetics and differentiation in-vitro of normal human uroepithelial cells on collagen gel substrates in defined medium. *J. Cell. Physiol.* 131: 285-301, 1987.

27. SCHUMANN, B. L., T. E. CODY, M. L. MILLER and G. D. LEIKAUF Isolation, characterization and long-term culture of fetal bovine tracheal epithelial cells. *In Vitro.* 24:211-216, 1988.

28. SPORN, M. B., G. H. CLAMON, and N. M. DUNLOP. Activity of vitamin A analogues in cell cultures of mouse epidermis and organ cultures of hamster trachea. *Nature.* 253: 47-50, 1975.

9. TSAO, M. C., B. J. WALTHALL and R. G. HAM. Clonal growth of normal human epidermal keratinocytes in a defined medium. *J. Cell Physiol.* 110: 219-229, 1982.

30. VOYTA, J. C, D. P. VIA, C. E. BUTTERFIELD, and B. R. ZETTER. Identification and isolation of endothelial cells based on their increased uptake of acetylated-low density lipoprotein. *J. Cell Biol.* 99: 2034-2040, 1984.

31. WU, R., and D. SMITH. Continuous multiplication of rabbit tracheal epithelial cells in a defined, hormone-supplemented medium. *In Vitro* .18: 800-812, 1982.

32. WU, R., and M. J. WU. Effects of retinoids on human bronchial epithelial cells: differential regulation of hyaluronate synthesis and keratin protein synthesis. *J. Cell Physiol.* 127: 73-82, 1986.

33. WU, R., E. NOLAN and C. TURNER. Expression of tracheal differentiated functions in serum-free hormone supplemented medium. *J. Cell Physiol.* 125:167-181, 1985.

We claim:

1. A method of isolating, from a heterogeneous population of lung cells, a lung cell line comprising a normal mammalian bronchiolar epithelial lung cell type, said cell line able to be maintained for multiple passages in the absence of serum without undergoing senescence, said method comprising the steps of:
   a) incubating mammalian lung fragments comprising said heterogeneous population of lung cells in serum free defined medium 11F; and
   b) changing said medium about every three days; and
   c) isolating said lung cell line from said serum free medium 11F, wherein the lung cells are not transformed with viral DNA during said method.

2. The method of claim 1 wherein said incubation period is between 10 and 90 days.

3. The method according to claim 2 further comprising:
   d) incubating said lung cell line in serum free medium 7F plus pituitary extract.

4. The method according to claim 3 further comprising:
   e) growing said lung cell line in serum free medium 11F plus pituitary extract.

5. The method according to claim 4 wherein said pituitary extract in bovine pituitary extract.

6. The method according to claim 4 wherein said mammalian lung is rat lung.

7. The method according to claim 4 wherein said mammalian lung is human lung.

8. The method according to claim 4 wherein retinoic acid is added to said serum free medium 11F plus pituitary extract at a concentration of about 0.05μ molar.

9. The method according to claim 1 wherein said mammalian lung is rat lung.

10. The method according to claim 1 wherein said mammalian lung is human lung.

11. A normal mammalian bronchiolar epithelial lung cell line produced by the method of claim 1.

12. The lung cell line according to claim 11 comprising a rat lung cell line.

13. The rat lung cell line according to claim 12 comprising cell line RL-65.

14. The lung cell line according to claim 11 comprising a human lung cell line.

* * * * *